United States Patent [19]

Ramani

[11] Patent Number: 4,982,500
[45] Date of Patent: Jan. 8, 1991

[54] INSTRUMENT FOR CUTTING OR GRIPPING

[75] Inventor: Rajendrakumar N. Ramani, Highland Park, N.J.

[73] Assignee: Five Star Idea, Inc., Highland Park, N.J.

[21] Appl. No.: 438,661

[22] Filed: Nov. 20, 1989

[51] Int. Cl.⁵ .............................................. B26B 13/00
[52] U.S. Cl. ....................................... 30/254; 30/257; 30/261
[58] Field of Search ................... 30/261, 262, 254–260, 30/234, 268, 269

[56] References Cited

U.S. PATENT DOCUMENTS

| | | |
|---|---|---|
| 598,593 | 2/1898 | Christensen et al. . |
| 681,740 | 9/1901 | Sansone . |
| 1,115,104 | 10/1914 | Prikla . |
| 2,093,987 | 9/1937 | Wallace .................................. 30/258 |
| 2,274,945 | 3/1942 | Van Keuren ...................... 30/254 X |
| 3,430,340 | 3/1969 | Perles . |
| 3,562,908 | 2/1971 | Rogers . |
| 3,608,565 | 9/1971 | Ensign . |
| 3,618,612 | 11/1971 | Ahn . |
| 3,721,245 | 3/1973 | Campbell . |
| 3,783,875 | 1/1974 | Wimshel . |
| 3,840,003 | 10/1974 | Kemlya . |
| 3,877,145 | 4/1975 | Andrews . |
| 3,899,829 | 8/1975 | Storm . |
| 3,914,866 | 10/1975 | Applegate . |
| 3,928,871 | 12/1975 | Wall . |
| 3,960,155 | 6/1976 | Wall . |
| 3,993,083 | 11/1976 | Torres . |
| 4,037,276 | 7/1977 | Brinker . |
| 4,140,124 | 2/1979 | Carutchet . |
| 4,271,838 | 6/1981 | Lasner et al. . |
| 4,285,344 | 8/1981 | Marshall . |
| 4,433,687 | 2/1984 | Burke et al. . |
| 4,644,651 | 2/1987 | Jacobsen . |
| 4,669,470 | 6/1987 | Brandfield . |

Primary Examiner—Douglas D. Watts
Attorney, Agent, or Firm—Mathews, Woodbridge & Collins

[57] ABSTRACT

The present invention is an instrument for cutting or gripping articles. The instrument comprises two shanks, with each shank having a handle end and a working end. The shanks are connected by at least two pivot means located between the handle and the working end of each shank. Each pivot means is secured into one or the other shank. The opposing shank has a channel through which each corresponding means passes. Preferably, the pivots and channels are located to close the working ends of each shank towards each other when the handles are pivotally rotated towards each other.

30 Claims, 5 Drawing Sheets

INSTRUMENT FOR CUTTING OR GRIPPING

The present invention is in the field of instruments for cutting or gripping; more particularly, the present invention relates to a scissor type instrument having a working end which can be used to cut or grip objects.

BACKGROUND OF THE INVENTION

Devices comprising two shanks connected at a pivot point, and having handle ends and working ends, are well known. Such devices include common scissors, surgical instruments and tools. The devices include forceps, needle holders, hemostats, medical cutters, lawn shears, and the like.

The patent art discloses many variations of this basic device. Such devices are disclosed in patents such as U.S. Pat. Nos. 3,430,340; 3,721,245; 3,877,145; 3,899,829; 3,783,875; 4,140,124; 4,271,838; 4,285,344.

Other patents of interest include U.S. Pat. Nos. 4,433,687; 4,770,174; and 4,644,651. Many of these scissor or cutting type devices comprise biasing means such as springs to hold them in an open or closed position. In a closed position the working ends of each shank are closed together. By an open position it is meant that the working shanks are separated. Generally the devices are open or closed by separating the handles and thereby separating the working ends through a pivot means.

U.S. Pat. No. 3,840,003 discloses a forceps assembly wherein working ends are brought together by a linkage member containing four pivoting arms.

U.S. Pat. No. 3,618,612 discloses a plier-type cutting or gripping tool having a first and second arm. In this particular apparatus the arms are pivoted at a single common pivot. The arms can be brought together by an additional lever pivotally connected to each arm.

U.S. Pat. No. 4,644,651 also discloses an instrument for cutting or gripping wherein two cutting jaws are pivotally connected at one pivot. Additionally, there is a levered mechanism pivotally connected to one of the arms to open or close the jaws.

U.S. Pat. No. 4,271,838 is another example of a suture cutter comprising a suture cutter, in combination with a spring, to maintain the suture cutter in the open position.

There are many types of gripping devices, such as hair gripping devices, disclosed in the art. Reference is made to U.S. Pat. Nos. 3,608,565; 3,960,155; 3,928,871; 3,993,083. Patents, such as U.S. Pat. Nos. 3,914,866; 681,740; 1,115,104; 598,593 disclose combinations of shears and combs.

SUMMARY OF THE INVENTION

The present invention is an instrument for cutting or gripping articles. The instrument comprises two shanks, with each shank having a handle end and a working end. The shanks are connected by at least two pivot means located between the handle and the working end of each shank. In preferred embodiments, there are two pivot means. However, there can be three or more. Each pivot means is secured into one or the other shank. The opposing shank has a corresponding channel through which each pivot means passes.

Preferably the pivots and channels are located to close the working ends of each shank in a direction toward each other when the handles are pivotally rotated towards each other. There is a first shank and a second shank, and the pivot means are preferably connected to the first shank and corresponding channels located in the second shank. In specific and preferred embodiments, there are handle means at the handle ends of each shank. There is a working member located between the working ends and the pivot means. The design of the working member can be varied. Preferably the working member is an elongated member with each working member having a working edge facing the opposing shank. The working edge can be formed into any suitable shape for cutting or gripping. The working edge can be serrated, sharp as in the case of scissors, flat for grabbing, or the working member can be specifically designed for a desired purpose, such as having at least one edge of the two shanks being a comb. The working members can be removably attached to the shanks with differently designed working members substituted.

The holding means are suitable for holding or gripping, such as finger loops or pressure surfaces. In specific embodiments, there can be a means, such as a spring, to bias the instrument so that the opposing working members are closed together, or alternatively, biased in an open position. There can be a means for locking the shank in any desired position from open to closed.

In preferred embodiments, the channels are designed to enable the opposing shanks to open and close as the pivots move through the channels. The channels enable the opposing shanks to move longitudinally and laterally with respect to each other. By design and location of the channels the opposing working edges can be opened further than when there is one pivot. Additionally, the relative angle between working members can be changed. A portion, preferably up to one-half of the channel length, and more preferably, less than one quarter, of each channel closest to the working edge is in a direction substantially parallel to a lateral axis through the instrument. This can enable opposing working straight edges be held open, and substantially parallel to each other.

The use of the specifically configured channels can result in an instrument where the opposing working members of the shanks can be varied relative to one another as the instrument is opened or closed. This is an advantage not heretofore recognized. For example, where one of the working members has a comb, the opposing working edges can be parallel to avoid the pulling of hair at the intersection of the two working edges which commonly occurs when there is only one pivot.

BRIEF DESCRIPTION OF THE DRAWINGS

FIGS. 10' and 10" are side views of FIG. 10.

DESCRIPTION OF THE PREFERRED EMBODIMENTS

The present invention will be understood by those skilled in the art by reference to the accompanying figures which show the preferred embodiments.

FIGS. 1-5 illustrate a preferred embodiment of the present invention which is an instrument for cutting or gripping articles. The instrument 10 comprises two shanks, a first shank 12 and a second shank 14. Each shank has a handle end and a working end. First shank 12, illustrated in FIG. 2, has handle end 16 and second shank 14, illustrated in FIG. 3, has handle end 16'. Each shank has a working end. First shank 12 has working end 18 and second shank 14 has working end 18'.

The two shanks are connected by at least two pivot means located between the handle ends 16, 16' and the working ends 18, 18'. The pivot means may be located in the first shank 12, the second shank 14, or at least one pivot means can be located in each shank 12 or 14. In the preferred embodiment, illustrated in FIGS. 1-5, all of the pivot means are connected to first shank 12. The pivot means in the embodiment of FIGS. 1-5, are pivots secured to the instrument 10 intermediate between handle end 16 and working end 18. Second shank 14 has corresponding channels which are located so that each pivot passes through the corresponding channel when the instrument 10 is assembled. The pivots and channels are located to close the working ends 18, 18' toward each other when the handle ends 16, 16' are pivotally rotated toward each other.

In an alternate embodiment the working ends 18, 18' can pivotally rotate away from each other when the handle ends 16, 16' pivotally rotate toward each other.

Figure 1:
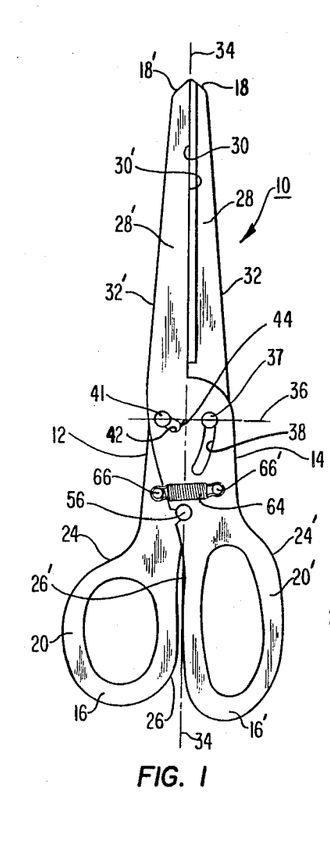
FIG. 1 is a preferred embodiment of the present invention containing three pivots and corresponding channels.
Figure 2:
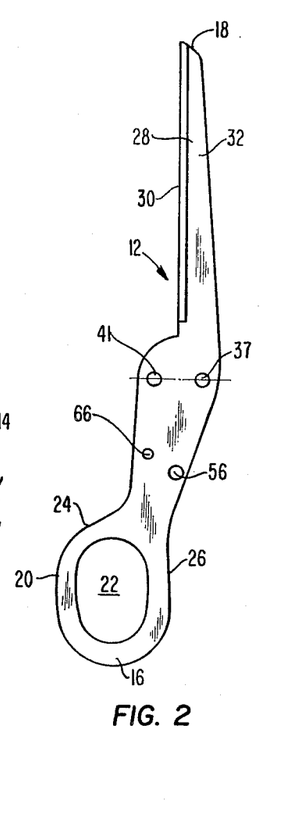
FIG. 2 is a plan view of the first shank in the embodiment of FIG. 1.
Figures 3, 5:
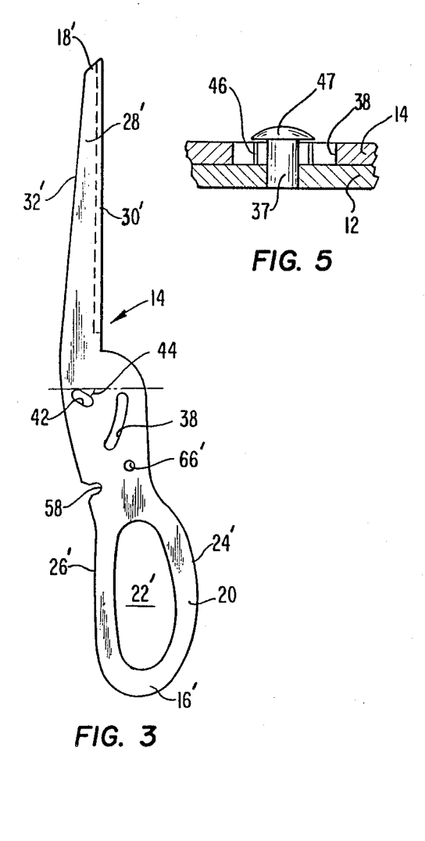
FIG. 3 is a plan view of the second shank in the embodiment of FIG. 1.
FIG. 5 is an enlarged sectional view of pivot 37 in channel 38.
Figure 4:
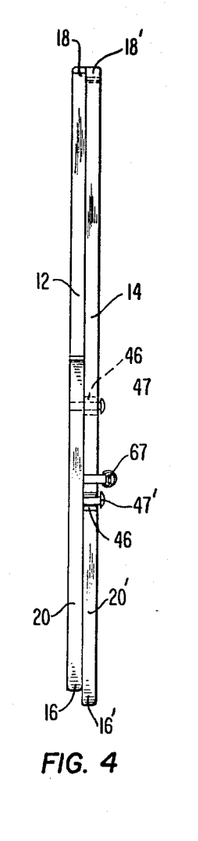
FIG. 4 is an edge view of the embodiment of FIG. 1.

The instrument has a handles 20 at the handle end 16 of first shank 12 and handle 20' at the handle end 16' second shank 14. In a preferred embodiment, the handles are finger loops 22 and 22' in first shank 12 and second shank 14, respectively. Any suitable means to hold the handle end can be used. Such means can include cylindrical handles, as well as suitable pressure surfaces, between the pivot means and the handle ends 16 and 16'. The handles further have outer handle edges 24 and 24'. These edges are on the side of the handle furthermost away from the opposing shank. That is, outer handle edge 24 of first shank 12 is on the side of first shank, away from second shank 14 upon assembly. Similarly, outer handle edge 24' is on the outside edge of second shank 14. Handles 20 and 20' have inner handle edges 26 and 26', in first shank 12 and second shank 14, respectively. Inner handle edge 26 is on the edge of the handle closest to second shank 14 upon assembly. Upon closing the instrument, inner handle edges 26 and 26' face each other, while outer handle edges 24 and 24' are opposite each other. Each shank 12 and 14 has a working member 28 and 28', which extends from the pivot means to the working end 18 and 18' of first shank 12 and second shank 14, respectively. Each working member 28 and 28' has a working edge 30 and 30', respectively. The working edges 30 and 30' face each other as the instrument is being closed.

Opposite the working edges are outer working member edges 32 and 32' in first shank 12 and second shank 14, respectively.

The location of the channels can be varied depending on the desired relative position of the working edges 30 and 30' during the opening and closing of the instrument. There are at least two pivot means located between the handle end and the working end of each shank. Each pivot means is secured in one of the shanks and passes through a channel of the other shank. One pivot means can be in first shank 12 and the corresponding channel in second shank 14, a second pivot means can be in second shank 14 and have a corresponding channel in first shank 12. In the preferred embodiment, illustrated in FIGS. 1-5, all of the pivot means are in first shank 12. The pivot means are located to permit rotation of the first shank 12 relative to the second shank 14 with the pivot means passing through corresponding channels in the second shank 14.

In order to describe the preferred location of the channels and pivot means reference will be made to a longitudinal axis 34 which is in a direction from handle ends 16, 16' towards the pivot means when the instrument is closed, as illustrated in FIG. 1. In the embodiment of FIG. 1, working members 28 and 28' are generally in the direction of longitudinal axis 34. The longitudinal axis is preferably centered between handle ends 16 and 16'. There is a lateral axis 36 perpendicular to the longitudinal axis. The lateral axis 36 passes through at least one of the pivot means.

In a preferred embodiment, there are at least two pivot means, each having a corresponding channel. There is a first pivot 37 passing through first channel 38. A second pivot 41 passing through second channel 42. First channel 38 and second channel 42, and the location of pivots 37 and 41, cooperate to determine the pivotal relationship between the first shank and the second shank. Preferably, there are at least two enclosed channels. That is, channels in which the pivot means remain during opening and closing of the instrument. This helps the operator stabilize the relative position of the two shanks. In a preferred embodiment, first channel 38 has a curved shape which will be called an arc. The arc generally is elongated in the longitudinal direction. The concave side of the arc faces longitudinal axis 34. The second channel 42 is generally shorter than first channel 38 and can be straight but is preferably curved. Second channel 42 preferably curves toward end 16' moving from edge 26' toward edge 24'. There is preferably a generally acute angle 44 between the second channel and the lateral axis 36. The acute angle 44 faces outer handle edge 24'. Preferably, up to 50 percent, and more preferably up to 25 percent, of the length of the channels nearest to the inner edge 26' are substantially parallel to the lateral axis 36.

In a preferred embodiment, the first pivot 37 and second pivot 41 are located along a common lateral axis 36. In an additional and preferred embodiment, a portion of each channel 38 and 42, closest to the inner edge 26', is substantially in a direction parallel to the lateral axis. In this embodiment, as the two shanks 12 and 14 are closed together, the working edges 30 and 30' become substantially parallel prior to the instrument being completely closed. This permits holding articles along the whole surface of the working edges rather than holding articles between two surfaces at angles emanating from a pivot, as is the case in common cutting scissors and holding scissors or pliers which rotate about a single pivot point.

The relative longitudinal and lateral location of the pivot means on instrument 10 can be varied as desired. Typically the pivot means are located between the lateral edges of the shank; and at least one, and preferably all of the pivot means, are located longitudinally from 10 to 90, and preferably 30 to 70 percent of the longitudinal distance from the handle ends to the working ends.

Preferably, the pivots are secured to the first shank 12. The pivots can be cylindrical pegs or posts which can be rotatably attached to the first shank 12, but are preferably integrally secured to the first shank 12 as shown in FIG. 5. There can be small cylindrical bearings 46 inserted around the posts to prevent wear and to facilitate the movement of the posts within the channels as the first shank and second shank 14 pivotally move relative to one another. There is a means to secure shanks 12 and 14 in opposing relation with the pivots in corresponding channels. In the embodiment illustrated in FIGS. 4 and 5, each peg passes through a corresponding channel. A cap 47, 47' is secured to the top of each peg. The height of the peg permits rotation of the opposing shanks 12 and 14. The cap is wider than the channel, preventing the opposing shanks from separating. Preferably, the caps are circular in a plane perpendicular to the axis of the pegs. The diameter of the circular cap is greater than the width of the channel.

In accordance with the preferred instrument of the present invention the working members 28 and 28' laterally separate at the pivot means upon pivotally rotating the first shank 12 and second shank 14 relative to one another. Depending on the configuration of the channels and their location, as well as the location of the pivots, the relative movement of the working edges 30 and 30' can be designed to meet particular needs.

In the embodiment of the present invention illustrated in FIGS. 1-5 there is a third pivot 56 and a third channel 58. This optional channel can be used to further direct the first shank 12 and second shank 14 relative to one another and to help maintain their position as the shank is closed. This is particularly useful where working edges 30 and 30' are substantially parallel immediately prior to being closed. The third channel 58 can be snug around pivot 56 in order to lock the instrument into a closed or nearly closed position as the elongated members 28 and 28' approach each other. The tightness of the channel 58 about pivot 56 can be adjusted to permit easy separation by hand. Channel 5( opens onto inner handle edge 26'.

The present invention car be varied depending on ultimate use. In the embodiments shown in FIGS. 1-5, the working edge is dull and the instrument can be used as a holding instrument and not a cutting instrument. Upon closure, the working edges 30 and 30' do not overlap. At least one of the working edges 30, 30' can have a flat surface, and the edges intersect when closed with the instrument being used as a holding means. In an alternate embodiment, the working edges can overlap and be sharp, and the apparatus be used in the manner of a scissor to cut articles.

FIGS. 6-13 illustrate alternate embodiments of the present invention.

Figures 6, 7:
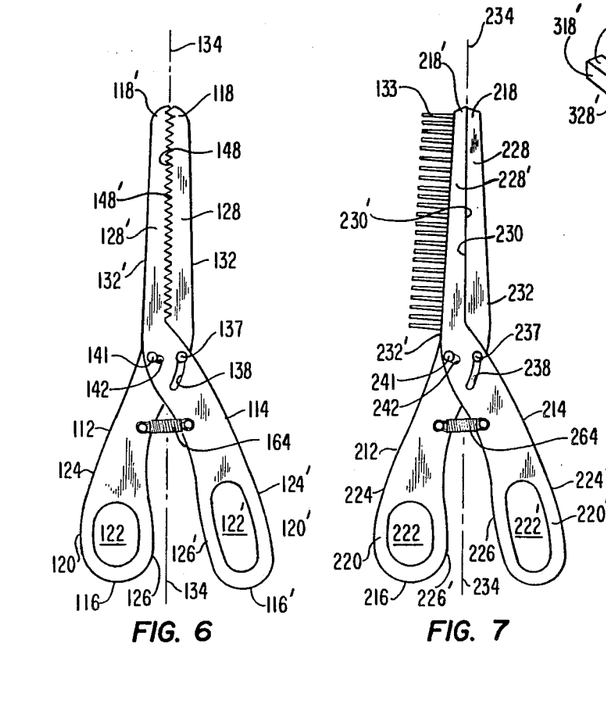
FIG. 6 is an embodiment of the instrument having two pivots and corresponding channels, and a serrated working edge.
FIG. 7 is an alternate embodiment of the instrument having a comb at one outer working member edge with the working edges forming a cutting scissors.

An alternate and preferred embodiment, is shown in FIG. 6. Elements in FIG. 6, common to those in FIGS. 1-5, have the same reference characters, plus 100. At least one of the working edges 148 or 148' can be serrated. This enables fibers to be held between the working edges.

In an embodiment, such as shown in FIG. 7, at least one of the outer working member edges 232 and 232' can have a comb means attached, such as comb 233, attached to edge 232', and the instrument used to hold hair during cutting or holding. Elements in FIG. 7, common to those in FIGS. 1-5, have the same reference characters, plus 200.

Figure 8:
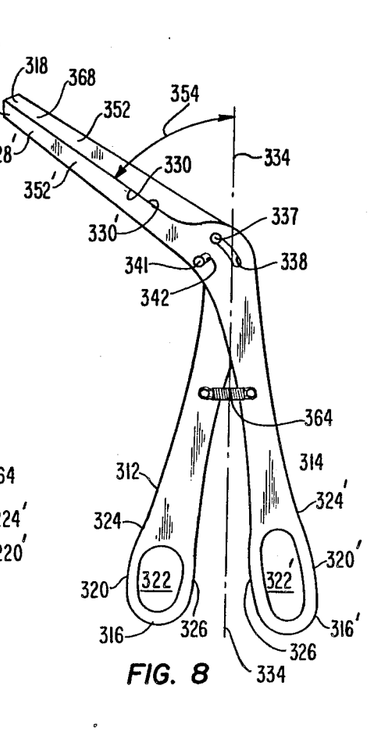
FIG. 8 is an alternate embodiment of the instrument where the elongated members are at an angle to the longitudinal axis through the handles.

FIG. 8, illustrates an alternate embodiment wherein the working members 352 and 352' are at an angle 354 to longitudinal axis 334. Elements in FIG. 8, common to those in FIGS. 1-5, have the same reference characters, plus 300.

The handles 20 and 20' can vary as desired. In the embodiment illustrated in FIGS. 1-8, the handles contain finger loops 21 and 22. Alternately, as noted above, and illustrated in FIG. 9, the handles can have pressure surfaces 460 and 460'. Elements in FIG. 9, common to those in FIGS. 1-5, have the same reference characters, plus 400.

The instrument 10 preferably has a means to bias the shanks 12 and 14 in an open or closed position. A preferred means is a spring 64, illustrated FIGS. 1-9. The spring is connected to the first shank and second shank by suitable means. In FIG. 1 each shank has a spring post 66 and 66'. The spring ends are looped over the posts. A suitable means, such as a spring cap 67, maintains the spring 64 in place. The spring 64, biases the handles 20 and 20' toward each other.

Figure 10:
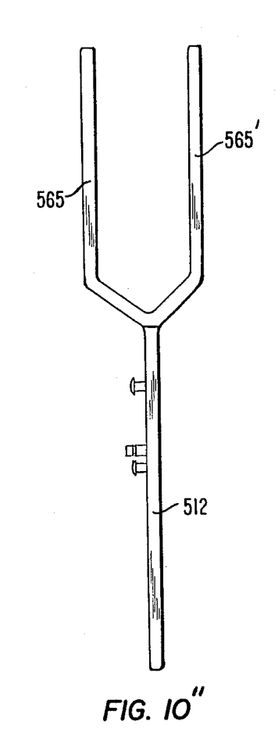
FIG. 10 is an alternate embodiment of the instrument where the opposing shanks have at least two elongated members.

In yet another embodiment, illustrated in FIGS. 10, 10' and 10" each of the opposing shanks, first shank 512 and second shank 514, has at least two elongated members 563 and 563' and 565 and 565' in a common plane at an angle, preferably perpendicular, to the plane through the longitudinal 534 and lateral axis 536. FIG. 10 has an alternate type biasing means, spring 564', which biases the working ends 528 and 528' apart. Elements in FIG. 10, 10', common to those in FIGS. 1-5, have the same reference characters, plus 500.

Figure 11:
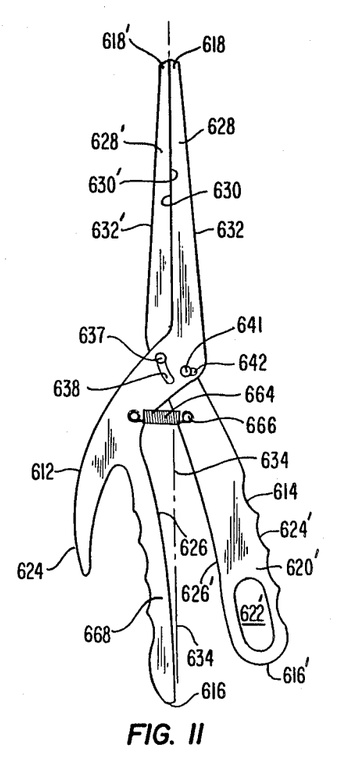
FIG. 11 is an embodiment further comprising one handle means for the thumb and the second handle means for the other fingers.

FIG. 11 is yet a further embodiment containing a handle means 668 and 668'. Such handle means 668 can maintain additional pressure on the instrument in the closed position. There is a finger loop 622 and handle 668. Elements in FIG. 11, common to those in FIGS. 1-5, have the same reference characters, plus 600.

Figure 12:
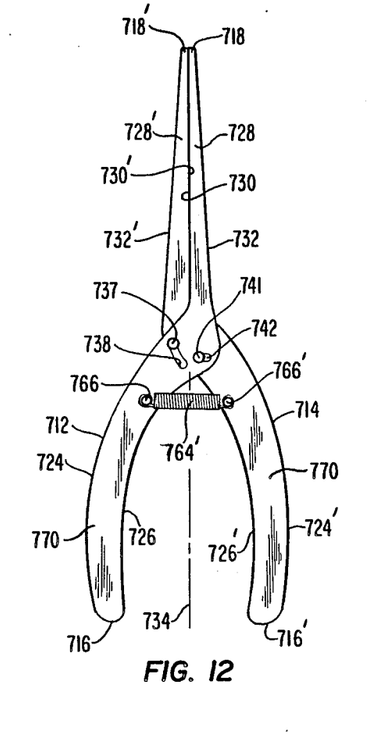
FIG. 12 is an embodiment useful as a needlenose pliers.

FIG. 12 illustrates an embodiment in the form of a needlenose pliers. Spring 764' forces handles 770 and 770' apart biasing working member 728, 728' to an open position. Elements in FIG. 12, common to those in FIGS. 1-5, have the same reference characters, plus 700.

Various embodiments of the present invention have a variety of uses including, but not limited to, holding and/or cutting fabric; paper; cardboard; sheets of leather, and plastic (polyvinyl chloride); craft materials;

wallpaper; shelf liners; hair; and twine and fibers, such as wool, thread sutures; and the like. The present invention is useful for household, commercial, industrial, hobbies, and medical/surgical applications, etc.

Figure 9:
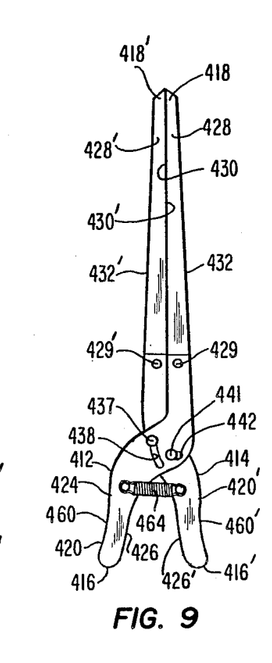
FIG. 9 is an alternate embodiment of the instrument where the handles have pressure surfaces.

In the various embodiments, such as shown in FIG. 9, at least one of the working members 428, 428' can be removably attached so that the same instrument can have a variety of uses. Part or all of the working members 428, 428' can be clipped or screwed into a working member base with screws 429 and 429'.

The examples set forth below illustrate the nature of the invention and the manner of carrying it out. However, the invention should not be considered as being limited to the details thereof.

EXAMPLES

Applicant has made two models. The first model corresponds to FIGS. 1-5. The models were made out of plastic sheet. The channels in the first model have the same shape and relative position as illustrated in FIGS. 1-5. Applicant has found that opening and closing the first model enables shank 12 and shank 14 to move longitudinally and laterally with respect to one another. Further, immediately prior to closing, the working edges 30 and 30' are much closer to parallel than when using a typical one pivot holding means.

Figure 13:
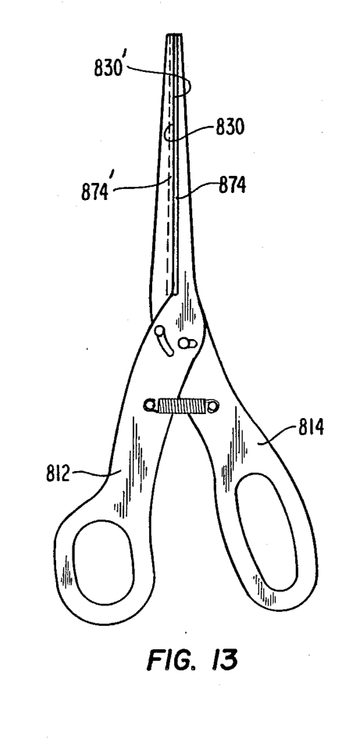
FIG. 13 is an instrument for which an example model was made.
Figure 14:
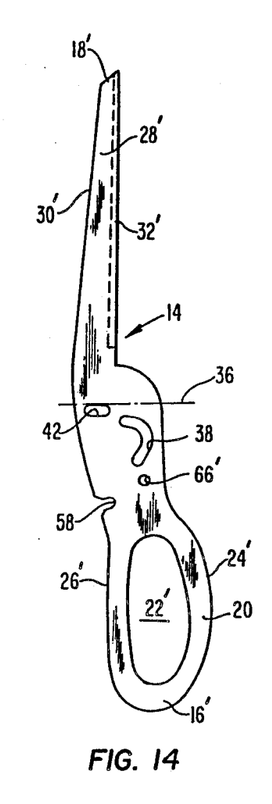
FIG. 14 is an alternate embodiment of the second shank shown in FIG. 3.

Applicant has made a second model similar to FIG. 13 with working edges 830 and 830' as flats 874, 874', glued onto the working edges. The flats were ⅛ inch wide and extended to full length of the working edge. The flats of opposing working edges 830 and 830' intercept each other. The biasing spring maintained the instrument in a closed position. The working edges were able to be much further apart when the instrument was completely opened than if there was one pivot between the two shanks 12 and 14. Other elements, shown in FIG. 13, correspond to those in FIGS. 1-5.

While exemplary embodiments of the invention have been described, the true scope of the invention is to be determined from the following claims.

I claim:

1. An instrument for cutting or gripping comprising: two shanks, with each shank having a handle end and a working end, the two shanks being connected by at least two pivot means located between the handle end and the working end of each shank, each pivot means secured in one shank and passing through a corresponding channel in the other shank, each shank having a working member located between the working end and the pivot means, the working member having a working edge facing the other shank, there being a longitudinal axis in a direction from the handle ends toward the pivot means when the instrument is closed, the longitudinal axis being between the handle ends, and there is a lateral axis perpendicular to the longitudinal axis, a portion of each channel being substantially parallel to the lateral axis of the instrument to enable opposing working edges to be substantially parallel prior to being closed.

2. The instrument of claim 1 wherein the pivots and channels being located to close the working ends of each shank toward each other when the handle ends are pivotally rotated toward each other.

3. The instrument of claim 1 wherein there is a first shank and a second shank and the pivot means are connected to the first shank and corresponding channels are located in the second shank.

4. The instrument of claim 1 wherein there is at least one first channel in the shape of an arc along the longitudinal axis concave to the longitudinal axis, and at least one second channel substantially in the lateral direction.

5. The instrument of claim 4 wherein the second channel extends toward the longitudinal axis and toward the handle end there being an acute angle between the second channel and the lateral axis.

6. The instrument of claim 5 wherein the second channel is substantially straight.

7. The instrument of claim 4 wherein the channels are located to permit rotation of one shank relative to the other with lateral separation of the shanks at the pivot means upon pivotally separating the shanks.

8. The instrument of claim 5 wherein there is a first pivot means and a second pivot means secured to the first shank along a common lateral axis.

9. The instrument of claim 1 wherein there is a handle on each shank located between the handle end and the pivot means.

10. The instrument of claim 9 wherein there is at least one first channel in the shape of an arc along the longitudinal axis having a concave side facing the working edges, and at least one second channel substantially in the lateral direction.

11. The instrument of claim 10 wherein the second channel is in the shape of a arc having the concave side facing the handle end.

12. The instrument of claim 9 wherein a portion of each channel closest to the working edge is substantially in a direction parallel to the lateral axis.

13. The instrument of claim 9 wherein the working edge is serrated.

14. The instrument of claim 9 wherein the working edges of opposing shanks are sharp.

15. The instrument of claim 9 wherein at least one of the working edges of the opposing shanks is flat.

16. An instrument for cutting or gripping comprising:
two shanks with each shank having a handle and a working end, the two shanks being connected by at least two pivot means located between the handle end and the working end of each shank, each pivot means secured in one shank and passing through a channel in the other shank,
each shank having a handle located between the handle end and the pivot means, and a working member located between the working end and the pivot means wherein the working member of each shank has a working edge facing the other shank and an outer working edge, and
wherein at least one working edge is a comb.

17. The instrument of claim 9 wherein the handle of each shank has a closing edge facing the other shank.

18. The instrument of claim 17 wherein there is at least one channel in the handle of at least one of the shanks and a corresponding pivot means disposed in the opposing shank.

19. The instrument of claim 18 wherein the channel in the handle opens at the closing edge of the shank.

20. The instrument of claim 9 where the elongated members are at an angle to the longitudinal axis.

21. The instrument of claim 9 wherein the handles have finger loops at the handle ends.

22. The instrument of claim 9 wherein the handles have pressure surfaces.

23. The instrument of claim 9 wherein each opposing shank has at least two opposing working members.

24. The instrument of claim 1 wherein the pivot means are posts.

25. The instrument of claim 24 wherein the posts are cylindrical posts connected to at least one of the shanks.

26. The instrument of claim 25 wherein the posts further comprise bearing means located between each post and the other shank.

27. The instrument of claim 1 further comprising a means to bias the shanks in an open or closed position.

28. The instrument of claim 27 wherein means to bias is a spring connected to each shank to force the shanks together in a closed position.

29. The instrument of claim 1 in the shape of a needlenose plier.

30. The instrument of claim 1 in the shape of scissors.

* * * * *